United States Patent [19]
Charlton et al.

[11] Patent Number: 5,208,163
[45] Date of Patent: May 4, 1993

[54] SELF-METERING FLUID ANALYSIS DEVICE

[75] Inventors: Steven C. Charlton, Osceola; Mihailo V. Rebec, Bristol; Catherine Ruetten, Granger, all of Ind.

[73] Assignee: Miles Inc., Elkhart, Ind.

[21] Appl. No.: 803,076

[22] Filed: Dec. 6, 1991

Related U.S. Application Data

[62] Division of Ser. No. 563,044, Aug. 6, 1990, Pat. No. 5,147,606.

[51] Int. Cl.⁵ .................... G01N 31/22; G01N 33/52
[52] U.S. Cl. .................................. 436/63; 436/165; 436/169; 436/178; 436/180; 436/807; 435/4; 435/810
[58] Field of Search ............... 436/52, 63, 165, 169, 436/171, 172, 177, 178, 180, 805, 807, 808; 435/4, 810

[56] References Cited

U.S. PATENT DOCUMENTS

| | | | |
|---|---|---|---|
| 4,256,693 | 3/1981 | Kondo et al. | 422/56 |
| 4,753,776 | 6/1988 | Hillman et al. | 422/101 |
| 4,756,884 | 7/1988 | Hillman et al. | 422/73 |
| 4,761,381 | 8/1988 | Blatt et al. | 436/165 |

FOREIGN PATENT DOCUMENTS

| | | |
|---|---|---|
| 0206561 | 12/1986 | European Pat. Off. |
| 0269240 | 6/1988 | European Pat. Off. |
| 0281201 | 9/1988 | European Pat. Off. |
| 0286371 | 10/1988 | European Pat. Off. |

Primary Examiner—James C. Housel
Assistant Examiner—David Redding
Attorney, Agent, or Firm—Roger N. Coe

[57] ABSTRACT

A method for detecting blood analytes with a sample volume as low as 2 microliters in the hematocrit range of 0% to 60%, or higher. This is accomplished by using a diagnostic device comprising a housing with various chambers and compartments for processing the blood. A sample application port in the housing is used to introduce blood into a metering chamber. From the metering chamber, the blood flows to a reaction chamber for analyzing blood analytes. Blood entering the metering chamber flows into a fluid capillary which indicates that an adequate amount of blood has been received in the metering chamber. The reaction compartment includes a reagent and a filter, the latter of which is disposed between the metering chamber and the reagent so that the reagent reacts with the filtered blood.

2 Claims, 2 Drawing Sheets

SELF-METERING FLUID ANALYSIS DEVICE

This is a division, of application Ser. No. 563,044, filed on Aug. 6, 1990, now U.S. Pat. No. 5,147,606.

TECHNICAL FIELD

The present invention relates generally to a device for analyzing blood and, more particularly, to a capillary device for analyzing blood using minimal sample volumes, e.g., fingerstick applications.

BACKGROUND ART

Many diagnostic tests are carried out in the clinical field utilizing whole blood as a sample. These diagnostic tests often employ techniques that include separating the serum or plasma from the whole blood and using that serum or plasma as a test sample to obtain an accurate reading of blood analytes, such as glucose, cholesterol, potassium, etc.

Traditionally, plasma and serum have been separated from whole blood by centrifugation. However, centrifugation is time consuming and requires equipment that is not generally available outside the clinical laboratory. Accordingly, field testing of the numerous blood substances that require the separation of serum or plasma is difficult.

A number of devices have been devised to address this problem. These devices generally utilize filtering devices capable of various types of blood separation. Such filters have been implemented using paper, non-woven fabric, sheet-like filter material composed of powders or fibers, such as man-made fibers or glass fibers, and membrane filters having suitable pore sizes. Known diagnostic devices that employ such filters include U.S. Pat. No. 4,256,693, Kondo, et al., which discloses a number of filter materials used to test blood in a multi-layered integral chemical analysis device. U.S. Pat. No. 4,477,575, Vogel et al., describes a composition and process for permitting the separation of plasma or serum from whole blood utilizing glass fibers in combination with other absorbent layers. U.S. Pat. No. 4,753,776 to Hillman et al. describes a device which separates serum from the whole blood and, using capillary force, moves that serum to a separate compartment in the device to perform the diagnostic chemical reaction.

These prior-art devices, unfortunately, have proven to be impractical or unsuitable for certain field applications. The patents to Kondo et al. and Vogel et al., for example, are unsuitable in applications which, due to space and volume constraints, require a small separation filter. Other problems associated with these prior-art techniques, including the patent to Hillman et al., involve a requirement for an excessive amount of blood, inadequate air venting for an accurate diagnostic reading of the reaction, an inability to handle excess blood, and/or they typically require the operator of the device to time or measure the amount of blood that is applied. These problems significantly hamper the diagnostic testing process. In many instances, added steps of measuring introduce intolerable delays.

DISCLOSURE OF INVENTION

In accordance with a preferred embodiment of the present invention, a diagnostic device for analyzing blood analytes includes a housing with various chambers and compartments that process the blood. A sample application port (located in the top, end or side of the housing) is used to introduce blood into a metering chamber. From the metering chamber, the blood flows to a reaction chamber for analyzing blood analytes. Blood entering the metering chamber flows into a fluid capillary which indicates whether or not an adequate amount of blood has been received in the metering chamber. The reaction compartment can include a first chamber area for containing a reagent and a second chamber area, disposed between the metering chamber and the first chamber area, for containing a filter. The filter separates the solid components from the blood and passes the filtered material to the reagent which effects the desired reaction.

BRIEF DESCRIPTION OF THE DRAWINGS

Other objects and advantages of the invention will become apparent upon reading the following detailed description and upon reference to the accompanying drawings, in which.

Figure 1:
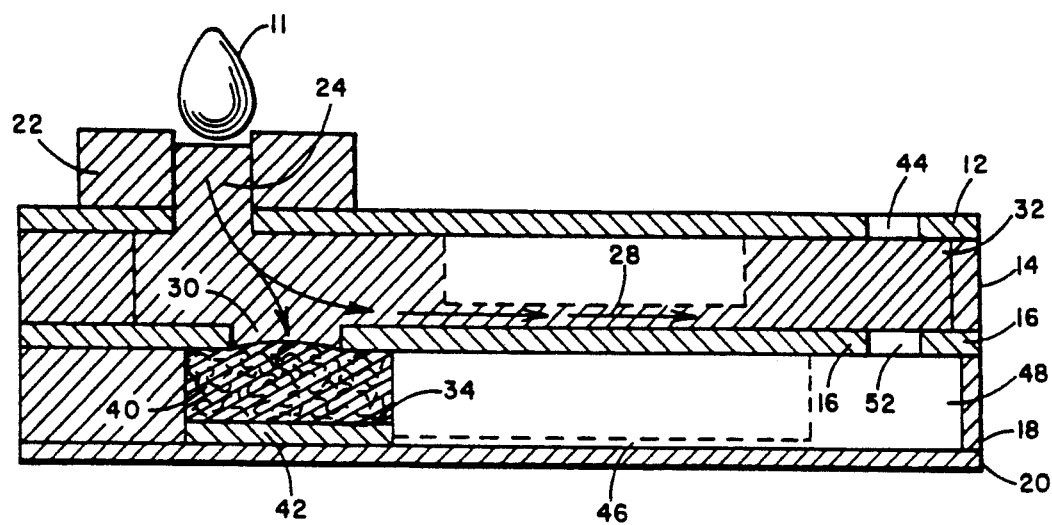
FIG. 1 provides a sectional view of a multi-layered blood analysis device, according to the present invention.

While the invention is susceptible to various modifications and alternative forms, specific embodiments thereof have been shown by way of example in the drawings and will herein be described in detail. It should be understood, however, that it is not intended to limit the invention to the particular forms disclosed. On the contrary, the intention is to cover all modifications, equivalents, and alternatives falling within the spirit and scope of the invention as defined by the appended claims.

DETAILED DESCRIPTION OF PREFERRED EMBODIMENTS

The present invention is particularly useful for detecting blood analytes with a sample volume as low as 5 micro-liters in the hematocrit range of 0% to 60% or higher. Such a minimum sample volume is typical in a fingerstick application. The above application is accomplished using a device that is constructed to provide a number of important advantages, including a self-metering function that allows the device to automatically indicate its blood sample volume requirement; thus, no timing or measuring of blood is necessary. In the following paragraphs, such a device is described in the form of a multi-layer laminate. It should be understood, however, that various other implementations could be used as well. For example, the device could be made using molded, cold-formed, and/or thermal-formed plastic parts.

FIG. 1 illustrates this layered device. It includes a laminated multi-layered housing 10 having a cover layer 12, a first adhesive layer 14, a capillary cover layer 16, a second adhesive layer 18 and a bottom window layer 20. Additionally, an application seat 22 is included adjacent to the cover layer 12. These layers, of course, are shown from a cross-sectional perspective.

The laminated housing 1 employs the application seat 22 to receive blood 11, e.g., from a pierced finger or applicator. The point at which the blood enters through the cover layer 12 is referred to as the application hole 24 of the laminated housing 10. The application hole 24 allows the blood to enter into a metering chamber 26, and, from the metering chamber 26, into a metering (fluid) capillary 28 and a reaction chamber or compartment 34. The blood enters the reaction chamber 34 via an access hole 30.

The metering chamber 26, the access hole 30 and the metering capillary 28 are constructed to provide the self-metering function referred to above. The access hole 30 is offset from the application hole 24 so that as blood fills the metering chamber 26, a predetermined amount of blood covers the access hole 30 before the blood is drawn into the metering capillary 28. This predetermined amount of blood provides the reaction chamber 34, located just below the access hole 30, with an aliquot of blood to effect the desired diagnostic reaction. Thus, once the metering chamber 26 has received the necessary amount of blood for the reaction, the metering capillary 28 responds by carrying excess blood to the containment chamber 32.

This self-metering arrangement provides at least two significant advantages. First, it provides proper balance in the removal of excess blood through the metering capillary 28. This allows the device to handle blood samples with high hematocrits (greater than about 50%). Additionally, because the metering capillary 28 quickly removes the blood from the metering chamber 26, the need for instrumental correction for hematocrit differences is avoided.

A second advantage concerns user convenience. For instance, the containment chamber 32 is designed to hold an excess amount of blood that is well beyond the minimum amount required for the reaction. This allows the operator to overfill the device with the sample blood and latently react to the overfilled condition. Also, the laminated housing 10, illustrated as transparent, can be colored so that the overfill/underfill status is readily recognized by sample color by the operator from a top or bottom perspective. Thus, once the operator sees blood in the metering capillary 28, or in the containment chamber 32, the overfill condition is present; conversely, before blood is seen in the metering capillary 28, an underfill condition is present, and additional blood is needed.

The design is sufficiently flexible to change sample volume by changing chamber and capillary dimensions.

With regard to the reaction chamber 34, it contains a filter 40 and a reagent membrane 42 (which can include one or more layers) to provide the desired diagnostic reaction. The filter 40 is preferably an absorbent glass fiber. The filter 40 and the reagent membrane 42 are placed in the reaction chamber 34 such that they maintain intimate contact with its walls to prevent leakage resulting in red blood cells coming in contact with the reagent membrane 42. The size and location of the access hole 30 also helps to minimize leakage. The filter 40 can protrude into the access hole 30, acting as a wick to pull the blood into the reaction chamber 34 before the blood is pulled via the metering capillary 28. When an absorbent glass fiber is used to implement the filter 40, the fiber surface should at least intimately contact the bottom surface of the capillary cover layer 16 for efficient absorption of the blood into the reaction chamber 34.

Another important advantage of the present invention involves the construction of the metering chamber 26 and the reaction chamber 34. The latter chamber provides filtration of red blood cells from the whole blood using a relatively small amount of blood. Moreover, when a glass fiber is used to implement the filter 40, plasma is virtually, completely separated from whole blood with or without the use of additives. The reagent membrane 42, which performs the analyte reaction mechanism (enzymatic/non-enzymatic), is capable of providing any needed final red cell separation.

The metering chamber 26 and the metering capillary 28 are sufficiently vented through air vent 44 to provide proper capillary flow and to allow the metering chamber 26 to be filled without trapping unwanted air. This is important, because, without such venting, capillary movement into the metering capillary 28 would not occur for high hematocrit samples.

Additional venting is provided by air capillary 46, located adjacent to the bottom window layer 20, to allow air venting directly from the reaction chamber 34. From the air capillary 46, air flows into an air chamber 48 and, if necessary, out through the containment chamber 32 and the air vent 44.

The venting of the metering and reaction chambers 26 and 34, as described above, is an important part of the operation of the device shown in FIG. 1. It is noted, however, that such venting can be accomplished in other ways. For example, venting of the reaction chamber 34 can be provided by employing a hole in the air chamber 48, through the bottom window layer 20 or through the second adhesive layer 18.

The air vents 44 and 52 can be manipulated in position and size to accommodate several purposes. For example, by making the diameter of the air vent 44 larger than the diameter of the air vent 52, no blood will flow from the containment chamber 32 into the air chamber 48. By reversing these diameter sizes, a relatively large amount of excess blood will enter the air chamber 48. If both the metering capillary 28 and the air capillary 46 are run directly to the edge of the device and out through the walls of the first adhesive layer 14 and the second adhesive layer 18, respectively, there is no need for the air vents 44 and 52.

It is noted that in FIG. 1, the dotted lines are included in connection with both the metering capillary 28 and the air capillary 46 to illustrate their capillary action from a cross-sectional view. The actual construction of these capillaries 28 and 46 is shown in detail in FIG. 2.

Figure 2:
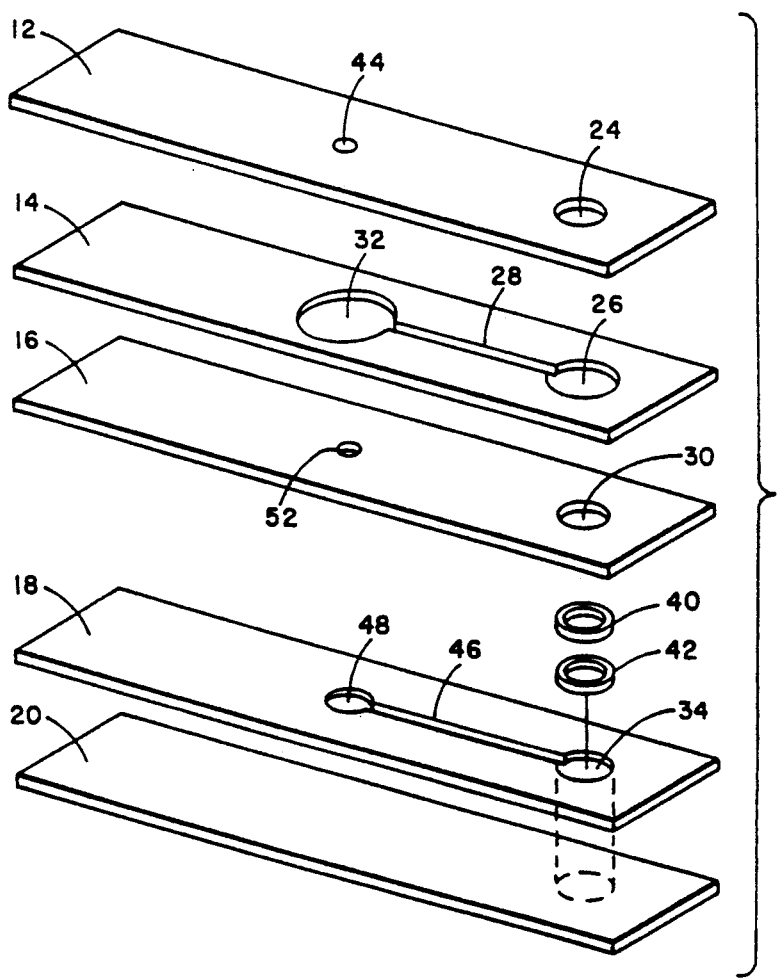
FIG. 2 provides a perspective view of the blood analysis device of FIG. 1 with its layers shown separated from one another.

Referring now to FIG. 2, the laminated multi-layered housing 10 of FIG. 1 is shown from a perspective view with the layers of the device separated. The dimensions of the layers can vary widely, but it has been found that a specific set of dimensions is particularly useful. These dimensions are set forth in the following paragraphs with reference to the device as shown in FIG. 2.

The cover layer 12 provides the application hole 24 and the air vent 44. The cover layer 12 is 2 inches (5.1 cm) long, 0.3 inch (0.8 cm) wide and 0.004 inch (0.01 cm) thick. The application hole 24 is about 0.2 inch (0.5 cm) in diameter, is centered with respect to the width of the cover layer 12 and is located 0.1 inch (0.3 cm) on center from the right side of the cover layer 12. The air vent 44 in the cover layer 12 is centered with respect to the width of the cover layer 12, is centered about 0.7 inch (1.8 cm) from the right edge of the cover layer 12 and is 0.1 inch (0.5 cm) in diameter.

The first adhesive layer 14, which provides the metering capillary 28 and the metering and containment chambers 26 and 32, also has a length of 2 inches (5.1 cm) and a width of 0.3 inch (0.8 cm). The metering chamber 26 and the containment chamber 32 are both about 0.3 inch (0.8 cm) in diameter, centered with respect to the width of the first adhesive layer 14 and interconnected by the metering capillary 28 which has a width of about 0.03 inch (0.08 cm). From the right side of the first adhesive layer 14, the metering chamber 26 is about 0.2 inch (0.5 cm) on center, and the containment chamber 32 is 0.6 inch (1.5 cm) on center.

The capillary cover layer 16 is constructed to provide the access hole 30 and the air vent 52, and a hydrophilic floor for the metering chamber 26 and the metering capillary 28. The capillary cover layer 16 is identical in length, width and thickness to the cover layer 12. The diameter of the access hole 30 is about 0.2 inch (0.5 cm). The access hole 30 is centered with respect to the width of the capillary cover layer 16, and may be offset from the application hole 24 of the cover layer 12 by about 0:1 inch (0.3 cm); thus, the access hole 30 is located 0.2 inch (0.5 cm) on center from the right side of the capillary cover layer 16. The air vent 52 is 0.1 inch (0.3 cm) in diameter, about 0.7 inch (1.8 cm) on center from the right side of the capillary cover layer 16, and also centered with respect to the width of the capillary cover layer 16.

The second adhesive layer 18, which provides the reaction chamber 34, the air chamber 48 and the air capillary 46, is identical in length and width as the previously discussed layers. The thickness of the second adhesive layer is about 0.01 inch (0.03 cm). The reaction chamber 34 and the air chamber 48 are both centered with respect to the width of the second adhesive layer 18, about 0.2 inch (0.5 cm) in diameter, and interconnected by the air capillary 46 which has a width of about 0.03 inch (0.08 cm). The depth of the air capillary 46 should be at least the depth of the filter 40, but can be as deep as the entire reaction chamber 34. From the right side of the second adhesive layer 18, the reaction chamber 34 is located about 0.2 inch (0.5 cm) on center, and the air chamber 48 is located about 0.7 inch (1.8 cm) on center. Both the reagent membrane 42 and the filter 40 are preferably about 0.2 inch (0.5 cm) (as determined by the elasticity of the material used) in diameter for a tight fit within the walls of the reaction chamber 34.

The bottom window layer 20 is preferably optically clear for instrument reflectance measurements on the reagent membrane. The bottom window layer 20 is 0.004 inch (0.01 cm) thick and may be implemented using the same length and width as the previously discussed layers.

Each of the layers 12, 14, 16, 18 and 20 is preferably composed of a plastic material, e.g., PET, to allow a view of the reagent membrane and, from either the top or the bottom sides of the device, a view of the metering capillary 28 and the containment chamber 32. The layers 12, 14, 16, 18 and 20 are preferably joined using a conventional double sided adhesive.

Figure 3:
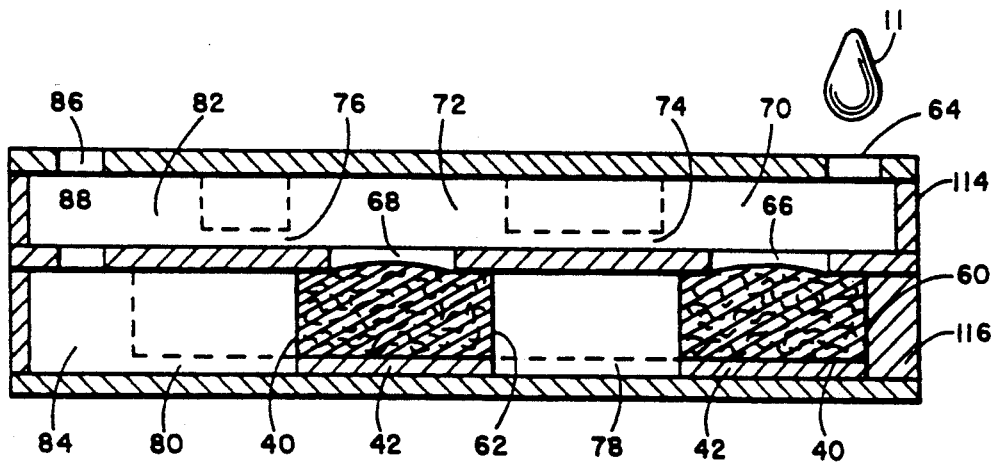
FIG. 3 provides a sectional view of an alternate multi-layered blood analysis device, also in accordance with the present invention.

Referring now to FIG. 3, a second embodiment for analyzing blood is shown, also in accordance with the present invention. The embodiment of FIG. 3 operates in a similar manner as the embodiment previously described in connection with FIG. 1 and FIG. 2. Unlike the previous embodiment, however, the embodiment of FIG. 3 provides two separate reaction chambers, first reaction chamber 60 and second reaction chamber 62. These separate chambers 60 and 62 are particularly useful for analyzing different blood analytes, e.g., glucose, cholesterol or a lipid panel. The embodiment of FIG. 3 includes an application hole 64, access holes 66 and 68, metering chambers 70 and 72, metering capillaries 74 and 76 and air capillaries 78 and 80 which operate in virtually the same manner as their counterparts in FIG. 1.

Blood is introduced through the application hole 64 into the first metering chamber 70 and, from the first metering chamber 70, into the first reaction chamber 60 and the first metering capillary 74, as previously described in connection with FIG. 1. When a sufficient amount of excess blood flows through the first metering capillary 74 into the second metering chamber 72, the process that took place in connection with the first metering chamber 70 is duplicated in the second metering chamber 72 and, via the access hole 68, in the second reaction chamber 62. The key difference between these two respective processes involves the filtering and reaction in the reaction chambers 60 and 62, which are of course defined by the filter and reagent membrane types that are used. Metering capillaries 74 and 76 indicate when their associated metering chambers 70 and 72 have received an adequate amount of blood.

The containment chamber 82, the air chamber 84, and the air vents 86 and 88 operate in the same manner as their counterparts in the embodiment of FIG. 1.

Figure 4:
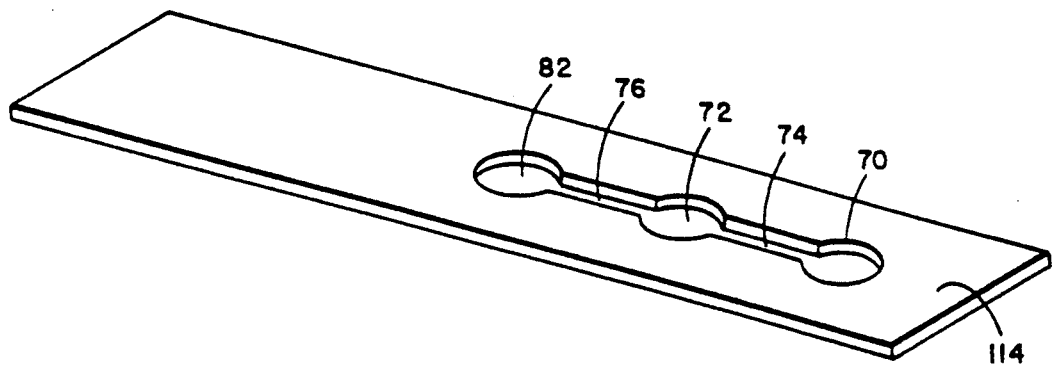
FIG. 4 provides a perspective view of the first adhesive layer 114 of the device of FIG. 3.
Figure 5:
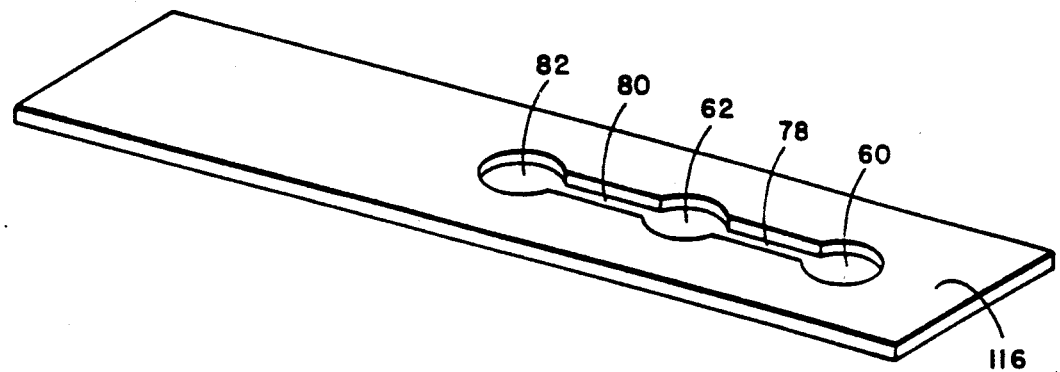
FIG. 5 provides a perspective view of the second adhesive layer 116 of the device of FIG. 3.

FIGS. 4 and 5 respectively illustrate the first adhesive layer 114 and the second adhesive layer 116 of the embodiment of FIG. 3 from a perspective view.

Accordingly, the present invention provides a unitized whole blood analyte assay strip useful for analysis with blood volumes as low 5 uL. The device does not require discrete operator metering or timing steps, and it provides complete sample containment of excess sample amounts. Moreover, the metering capillary provides visual detection (human or instrumental) of an overfill or underfill condition and avoids the need for instrumental correction for hematocrit differences.

While the invention has been particularly shown and described with reference to multiple embodiments, as mentioned above, it will be understood by those skilled in the art that various other modifications and changes may be made as well. For example, the previously described embodiments can be modified to include several reaction chambers in a linear or radial array to allow for multiple blood analyte determinations using one drop of blood. Also, it is possible to have the application seat flush with the cover layer. For example, the cover layer could have a rounded depression which would constitute the application seat to receive blood. In addition, the application seat could be located on a side or on the end of the laminated multilayered housing for introduction of blood. This would permit the end loading or side loading of blood into the metering chamber. Such modifications and changes do not depart from the spirit and scope of the present invention which is set forth by the following claims.

We claim:

1. A method for analyzing fluid, comprising the steps of:
    introducing a sample of fluid into a test device which directs the fluid to a metering chamber that further directs excess fluid to a fluid capillary once the metering chamber has received an ample amount of the fluid;

directing an aliquot of said fluid from the metering chamber to a reaction chamber;

filtering the fluid in the reaction chamber and then directing the filtering fluid into contact with a reagent.

2. A method for analyzing fluid, according to claim 1, further including the step of directing excess fluid into a fluid containment chamber from the fluid capillary.

* * * * *